United States Patent [19]

Barten et al.

[11] 4,226,540
[45] Oct. 7, 1980

[54] METHOD FOR THE CONTACTLESS DETERMINATION OF FEATURES OF MEAT QUALITY

[75] Inventors: Hans M. Barten, Friedberg; Frieder K. H. Pfister, Augsburg, both of Fed. Rep. of Germany

[73] Assignee: Pfister GmbH, Fed. Rep. of Germany

[21] Appl. No.: 919,872

[22] Filed: Jun. 26, 1978

[30] Foreign Application Priority Data

Jun. 25, 1977 [DE] Fed. Rep. of Germany ....... 2728717

[51] Int. Cl.³ .......................................... G01N 21/55
[52] U.S. Cl. ................................. 356/445; 356/237
[58] Field of Search ........................... 356/445, 237

[56] References Cited

U.S. PATENT DOCUMENTS

| | | | |
|---|---|---|---|
| 3,154,625 | 10/1964 | Kail | 356/445 |
| 3,396,280 | 8/1968 | Knudsen | 356/445 |
| 3,620,630 | 11/1971 | Hergenrother | 356/237 |
| 3,795,452 | 3/1974 | Bourdelais et al. | 356/237 |
| 3,877,818 | 4/1975 | Button et al. | 356/445 |

*Primary Examiner*—Vincent P. McGraw
*Attorney, Agent, or Firm*—Hill, Van Santen, Steadman, Chiara & Simpson

[57] ABSTRACT

A method and apparatus is disclosed for the contact-free determination of features of quality of a test object selected from meat products. In one embodiment the test object is radiated with a light source. Radiation emanating from the test object is detected to create definite radiation values. These definite radiation values are then analyzed, preferably in comparison to the reference values. In another embodiment, a scanning device is employed for the production of a scanning ray. The scanning ray is deflected over the test object and a detector is employed for determining characteristics of points on the test object scanned by the scanning ray. With the method and apparatus disclosed, quality features such as the fresh condition, color and meat/fat ratio of the meat may be determined.

4 Claims, 5 Drawing Figures

METHOD FOR THE CONTACTLESS DETERMINATION OF FEATURES OF MEAT QUALITY

BACKGROUND OF THE INVENTION

The invention relates to a method as well as an apparatus for the contactless determination of the quality of a test object in the category of meat products, particularly of a butchered animal carcass, parts thereof, or of a product derived essentially therefrom.

Methods and devices for the determination of the condition of foodstuffs are known, for example for the determination of the condition of freshness of fish, in which the ratio of the electric resistances of a fish is determined for two different measuring frequencies, for example.

Another method which works according to a similar physical principle has become known through the German Laid Open Specification No. 2,007,964, which states the conditions for dependence between the fresh condition of foodstuffs and their electrical characteristics, or between the fresh condition and a combination of different electrical characteristics of the corresponding foodstuff, respectively.

Foodstuffs considered here are fish, meat, poultry, vegetables, fruits as well as a number of other foodstuffs as long as they have a cell structure, such as milk and eggs. In addition, liquid foodstuffs, such as, for example, alcoholic beverages, are also considered.

In the known method, the test object is superficially manually scanned with a probe head which is equipped with circularly shaped electrodes arranged concentrically within one another. The relative dielectric constant or the specific resistance of the probe is measured. With the device, the object is to maintain quality-control of foodstuffs, for example, for the determination of the fresh condition, inexpensively and rapidly yet without carrying out the extraction of a sample.

Furthermore, different other methods and apparatus have become known for the determination of the weight by volume of meat wares and/or for the determination of their fat content. (for example Laid Out Specification No. 1,598 and Laid Out Specification No. 1,937,573.)

In these known methods and apparatus, after extraction of a sample, for example in the case of meat and sausage products, the sample is compressed a predetermined amount, the volume measured, the sample weighed, and through comparison of weight and volume, its fat content determined.

Such known testing methods and apparatus have in common the disadvantage that they can only be carried out by intimate contact with the test object or parts of the same, or with the extraction of a sample from foodstuffs, it is absolutely essential that the sample be discarded after the test.

By the utilization of probes which, for example, must be brought into definite electrical contact with the surface of the test object, or by puncturing with needles into the depth of the object, it is regarded as a particular disadvantage that on the one hand such apparatus or apparatus parts must be carefully cleaned after each use, and on the other hand, the contact betwween probe and test object creates an uncertainty factor which, even with the greatest care, cannot reliably be brought under control. Therefore, the result is not free from errors and risks, and supplies at best individual values at points and therefore still inaccurate individual values because of their dependence upon manipulation.

Unfortunately, in the case of foodstuffs, in spite of the existence of definitions as to the classification of goods, the classification into the different classes of goods is handled individually and therefore differently by experts, and with subjective judgment having wide dimensions of discretion. This results in economic loss.

SUMMARY OF THE INVENTION

An object of the present invention is to improve the state of the art by means of a method and an apparatus which insures the determination of definite characteristics of quality for a test object taken from foodstuffs, particularly in the category of meat wares. The tests are free from contact with the test object and above all do not require extraction of samples for treatment during the testing operation.

The operation is also rapid and uncomplicated. The test method as well as the apparatus can be automated to the fullest extent in order to be free from subjective margins of judgment which results in a reproduceable result as free from errors as possible.

With the invention, the problems discussed above are solved in that the radiation emanating, emitted or reflected from the object or at least from one field of the object is advantageously detected at least partially in the visible or invisible range of light, and is evaluated in reference to the definite physical values of radiation, such as the wave-length and/or the intensity and/or the polarization.

In an embodiment of the method, definite values and reference values may be correlated with tolerance ranges, whereby within a predetermined margin of tolerance, ranges of value and/or ranges of reference value are included.

The extent of such a margin of tolerance is to be predetermined from case to case. For each type of sample, quality feature and demand are determined by specially trained personnel or according to the experience of a statistical average of a plurality of results.

Furthermore, with the method according to the invention, the procedure may be such that the average representative of medium value amount of a radiation value is determined for the object or the field, respectively.

Also, especially in the case of the desire for more specific results, the procedure may be such that specific radiation values or ranges of radiation value may be determined as to different parts of the object or of the field, respectively.

Advantageously in this connection, the measuring values or ranges of measuring value of correlated parts of the object or of the field may be determined and their surfaces summed up.

In a development of the method, the surfaces correlated with a determined measuring value or range of measuring value may be compared with the sum of values of the surfaces correlated with another mesuring value or range of measuring value.

In many cases, it is also of advantage to make use of the alternative measure that a determined value or range of value is compared with at least one predetermined reference value or range of reference value.

In order to make this procedure possible in a meaningful manner, a reference value or range of reference value is determined by means of measuring of a radiation emanating from at least one reference field.

This may advantageously be carried out such that as a reference field, a background surface projecting beyond the contours of the object, or a base or a mask forming a border around the field to be measured, it utilized.

In this connection it is further suitable in the invention to correlate definite features of quality of the object with definite reference values or reference value ranges.

A practical manner of carrying out the method according to the invention consists in that the object is radiated with a radiation of definite type, advantageously with light, and that a picture is projected from the object with optical means. The radiation of the picture is detected and evaluated in reference to definite physical radiation values or ranges of radiation value.

In most practical cases, it is sufficient that as a definite type of a radiation a light radiation is advantageous, and its color spectrum and/or brightness and/or polarization is evaluated.

Another likewise practical and advantageous embodiment of the method consists in that the object is scanned with a focused, movable scanning ray, preferably according to lines or rasters.

For this, one may, for example, utilize the scanning ray of a light-gun with a deflecting characteristic, for example of a line-raster, in order to produce on the object or object field in the course of the line raster a plurality of points of light of different brightness, whose brightness value is received by a detector and converted into electric signals.

It may, however, also be possible in special cases to utilize heat radiation as an emitted radiation of the object.

If use is made of the phenomenon that the gradient of a temperature change, for example a temperature decrease with different condition of cell groups, attains different values in the test object, then it is possible to separate, for example, fatty tissues from meat or muscle tissue with the aid of the emitted heat radiation of a corresponding object, if the object at the same time is subjected to a temperature change. Possibly in this connection diseased changes of tissue parts may also be recognized and localized.

In an economical embodiment of the invention, generally light is preferred and different types of light may be used.

Thus, for example, in cases for the determination of fresh condition, an illumination of the object with monochromatic light is provided. The object is illuminated with light having a definite wave range out of the spectrum of the electromagnetic light-wave range or with polarized light, that is, with light which swings only in a preferred plane of the electromagnetic field. A light of different brightness, that is, of different intensity, may also be provided. The illumination leads to a series of evaluations with absolute character supporting one another in the evidence. Especially advantageous for the same are comparative measurements in different wave ranges of the light.

With the different features of quality which are to be determined by means of the invention, for example with analysis of a swine-half, preferred importance is attributed to the so-called meat/fat ratio.

A further feature of quality essential for the importance of the invention is fresh condition.

As a further feature of quality, for example, upon the adjudication of determined types of meat, as for example, chicken meat or calf meat, the shade of coloring of the test object is of importance.

And finally, a further feature of quality to be taken at least in an auxiliary manner into consideration is the geometric dimension of the object which is determined at least in one plane of consideration, or, as the case may be, in two planes of consideration.

In this connection, the procedure may be such that for determination of the dimensions, the contours of the object are received in optical manner and by means of known electronic conversion and transfer means, are recorded on any desired information carrier.

With a further embodiment of this measure, the procedure may be such that from an illustration of the contour, the content of the surface surrounding the same is calculated.

An apparatus for carrying out the method comprises a device for the production of an advantageously high-frequency scanning ray, for example, a light-gun. A controllable device for the deflection of the ray into two planes, advantageously in form of line-rasters, as well as at least one detector for the determination of the brightness value of the point of light reflected by the object are also provided. An electronic device for the conversion of brightness values into electrical signals, a converter for the transforming of the electrical signals into digital electronic signals, preferably into impulses for the entry into a computer, a computer and memory unit, and at least one signal delivery unit attached to the computer are also provided.

In a preferred embodiment of the apparatus, the computer unit is equipped with an output for a control signal which is effectively connected with the control of the deflection device.

With this device, it is possible to correlate the brightness value of a point of light with its place in the field and thereby to obtain and imaginary picture of the test object or object field and then to store the obtained picture in the computer unit. With a corresponding computer program, one is accordingly in a position to determine surfaces or partial surfaces of the object corresponding to different brightness values or brightness-value ranges, for example, and to sum up the same and compare them with one another.

If, for example, the scanned test object consists of fatty portions and meat portions, then in this manner, through evaluation of such optical-electronic signals, the surface ratio of fat and meat, the so-called fat/meat ratio, may accurately be determined.

With the afore-described apparatus, it is essential for the attainment of values free from difficulty, that both the measuring object as well as also at least the optical part of the apparatus be arranged in a darkened room, preferably with non-deflecting walls.

In other cases, by means of an incidence of foreign light or reflection of stray light, a falsification of the results would not reliably be excluded.

In a further embodiment of the apparatus, instead of or in addition to the brightness detector, the arrangement of further detectors may be provided for the detecting of color tones and their conversion into electrical signals.

In many cases, for a condition of the sample characterized by means of color values from which conclusions may be drawn as to features of quality, for example with respect to the condition of freshness, it is of importance to consider the object through a color detector in a preferred area of the spectrum.

In order to make this possible, in the apparatus of a further embodiment, there is arranged between the scanning ray and the object at least one color filter. There may also be arranged further exchangeable color filters, whereby the individual color filters are determined advantageously with respect to one another with respect to limits in the color spectrum.

An arrangement modified in relation to the foregoing apparatus described, has a definite source of light for the illumination of the object or the object field, respectively. An optical system for the ray deflection and bundling, an electro-optical device for the measuring of brightness- and/or color-tone values, a Vidicon-type camera with an output for picture signals, and an attached electronic part with signal-converter, calculator, delivery and control unit somewhat analogous to the electronic part of the apparatus described in the foregoing, are also provided.

Also, this apparatus which corresponds in function and structure for example to a television pick-up camera, may preferably employ at least one color filter between the source of light and the object.

Alternatively, the apparatus, however, may also have a color filter between object and camera.

With such an arrangement, it may be of advantage to exchangeably arrange several color filters by a motor-driven remote servicing.

Finally, the photography device may be a color-camera, preferably of the video-electronic type.

DESCRIPTION OF THE PREFERRED EMBODIMENTS

Figure 1:
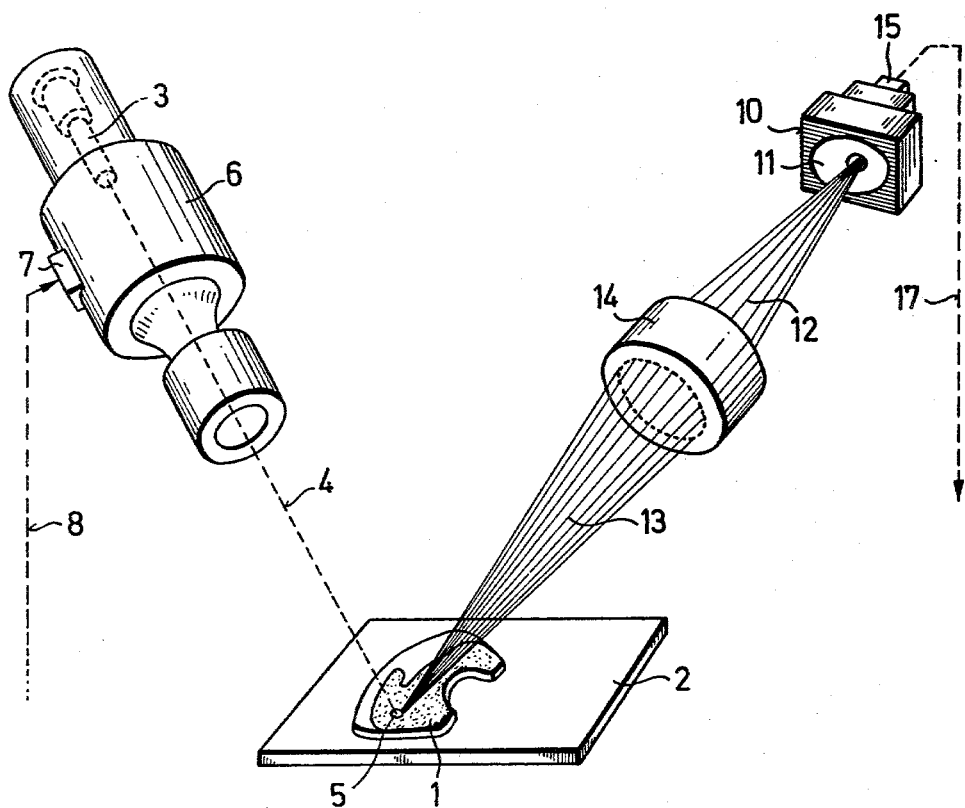
FIG. 1 diagrammatically illustrates the scanning of an object with a scanning ray and receiving of the brightness-values by means of a bright/dark receiver.

In FIG. 1 is located the object 1 to be determined and ready to be measured, for example, a piece of meat, on a neutral base 2. The object 1 is irradiated by a light gun 3 with a ray 4 of light. The latter produces on the surface of the object 1 the point of light 5. The light gun 3 is equipped with a pair of deflection coils 6, which deflect the scanning ray 3 in two planes in such manner that the latter describes a pattern of movement in the form of a zig-zag line raster, a technique previously known. The control of the deflection coils takes place through control of the coil input 7, whose effective connection 8 with the control unit 9 is apparent in detail from the block diagram of FIG. 3.

The arrangement according to FIG. 1 further comprises the bright/dark detector 10, which, for example, is equipped with a selenium-coated receiver plate 11. The optical course of rays 12, 13 between the point of light 5 and the receiver plate 11 is conveyed through an optical device 14 which bundles the incidence of light of the reflection of the point of light 5 to the bright-dark detector 10 and thereby optically reinforces. This optical device 14 consists, for example, of a plurality of lenses combined in an objective or lens, with definite or with adjustable focal length, repectively, as is known in the broadest sense from the photographic pick-up art. The output 15 of the bright/dark detector 10 is in effective connection with the electronic control and computer unit 18 shown in the block-diagram of FIG. 3, and particularly through the conversion unit or converter 16. The connection between the outlet 15 of the bright-/dark detector 10 and the converter 16 is indicated at 17. The converter 16 is in effective connection with the computer unit 18 through the connection line 19. With the computer unit 18, which has an integrated memory unit, therein, there is connected on the one hand the control unit 9 for control of the deflection coils 6 through the control line 20, and on the other hand the output unit 21 through the connection line 22.

Figure 3:
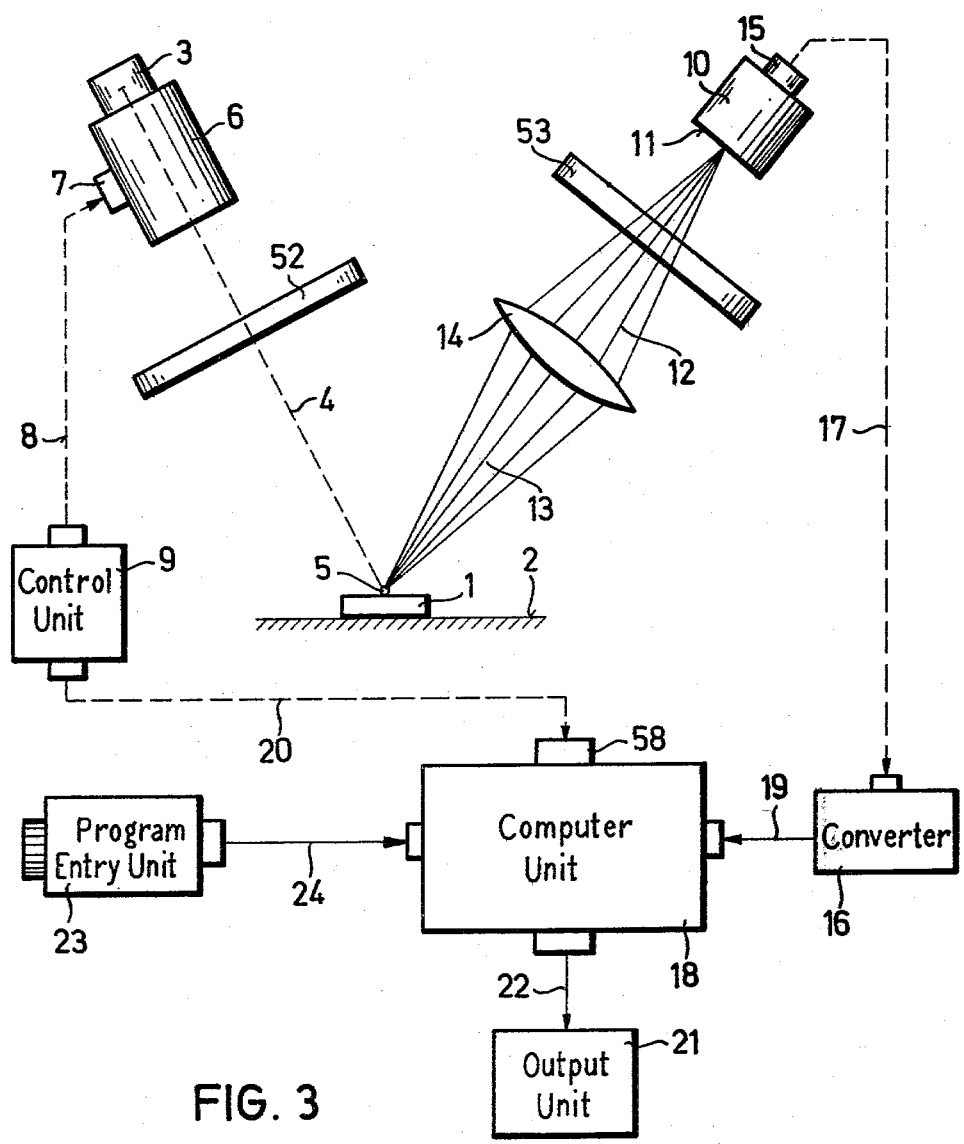
FIG. 3 shows a block diagram of the arrangement according to FIG. 1 with an electronic evaluation device.

The principle and function of this apparatus as set forth in FIG. 1 and block diagram FIG. 3 is as follows.

Figure 5:
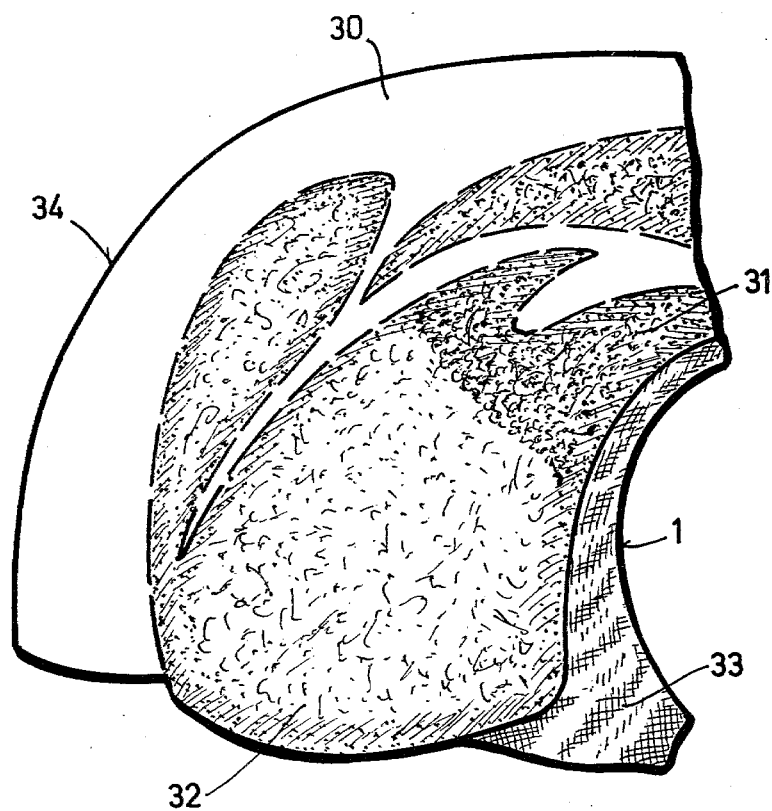
FIG. 5 shows the illustration of a test object in plan view.

As a prerequisite for the explanation of this function, for example an object 1 is provided for which a determination of the fat/meat-ratio is desired. The object 1 is in this example a porkchop. It consists, according to the illustration in FIG. 5, of an essentially closed fat portion 30 and more or less fissured particles of meat 31 which include a somewhat brighter inner meat portion 32 rippled throughout with portions of fat, as well as a bone portion 33 and a rind 34.

This test object according to FIG. 1 is scanned by the light gun 3 with the light point 5 according to a line-raster, whereby the guidance of the light ray 4 is scanned with the aid of the deflection mechanism of the deflection coil pair 6 controlled by the control unit 9. In this connection, the intensity of the reflection is different as a result of the difference in the condition of the surface of the test object 1. Therefore, the reflection of the individual points of light 5 according to place of encounter appear brighter or darker. These points of light 5 are projected with the aid of the lens 14 to the receiving surface 11 of the bright/dark detector 10, and with the aid of this device, are converted according to the rate of their brightness value into electrical signals, for example of different voltages. The latter appear at the output 15 of the detector 10 and are introduced through the connecting line 17 into the converter 16. This converter 16 converts the electrical starting signals of the detector 10 into computer-compatible input signals, which are supplied into the computer 18. Into the computer 18 at the same time there are supplied by the control unit 9 through the connection line 20 the positions pertaining to each point of light of the point of light on the object 1, so that in the computer unit 18, an imaginary picture of the object 1 consisting of light impulses and correlated electrical orientation data is received.

With the aid of a program entry unit 23 which connects by collection line 24 with the computer unit 18, different programs may be entered into the computer 18 from which the latter is set in position for evaluation of the received electrical signals as radiation values and orientation data, for example to sum up the radiation the brighter surfaces as a first group correlated with the fat portions 30, as well as to sum up radiation values from the darker surfaces as a second group correlated with the meat portions 31, and to compare the surface sums with one another and, for example, to express the same directly in percentages.

This indication may be shown in the output unit 21 in the form of figures such as for example in percentage values. It may, however, also be further transferred to a printing unit, to perforated tapes or other data-carriers, or absolute values of the surfaces may be calculated.

The degree of evaluation by computation as well as the fine definition of the point-form solution of the entire object surface is in this connection subjected to no limitation.

Figure 2:
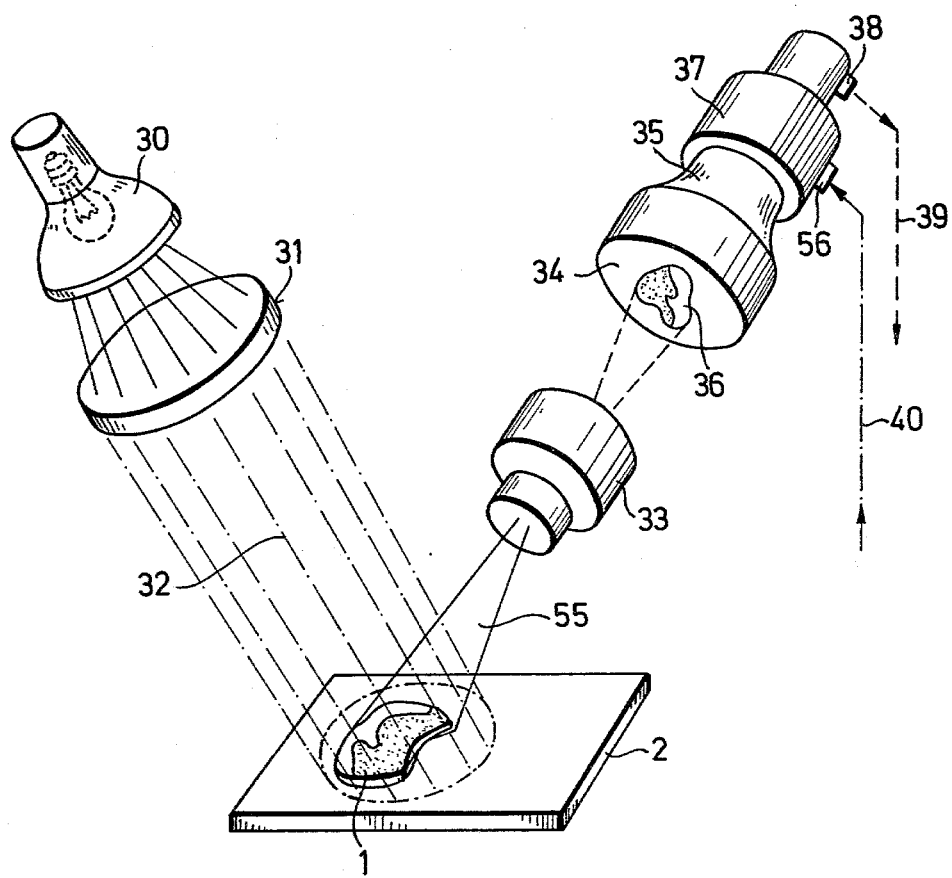
FIG. 2 shows an arrangement with a source of light and a Video camera.
Figure 4:
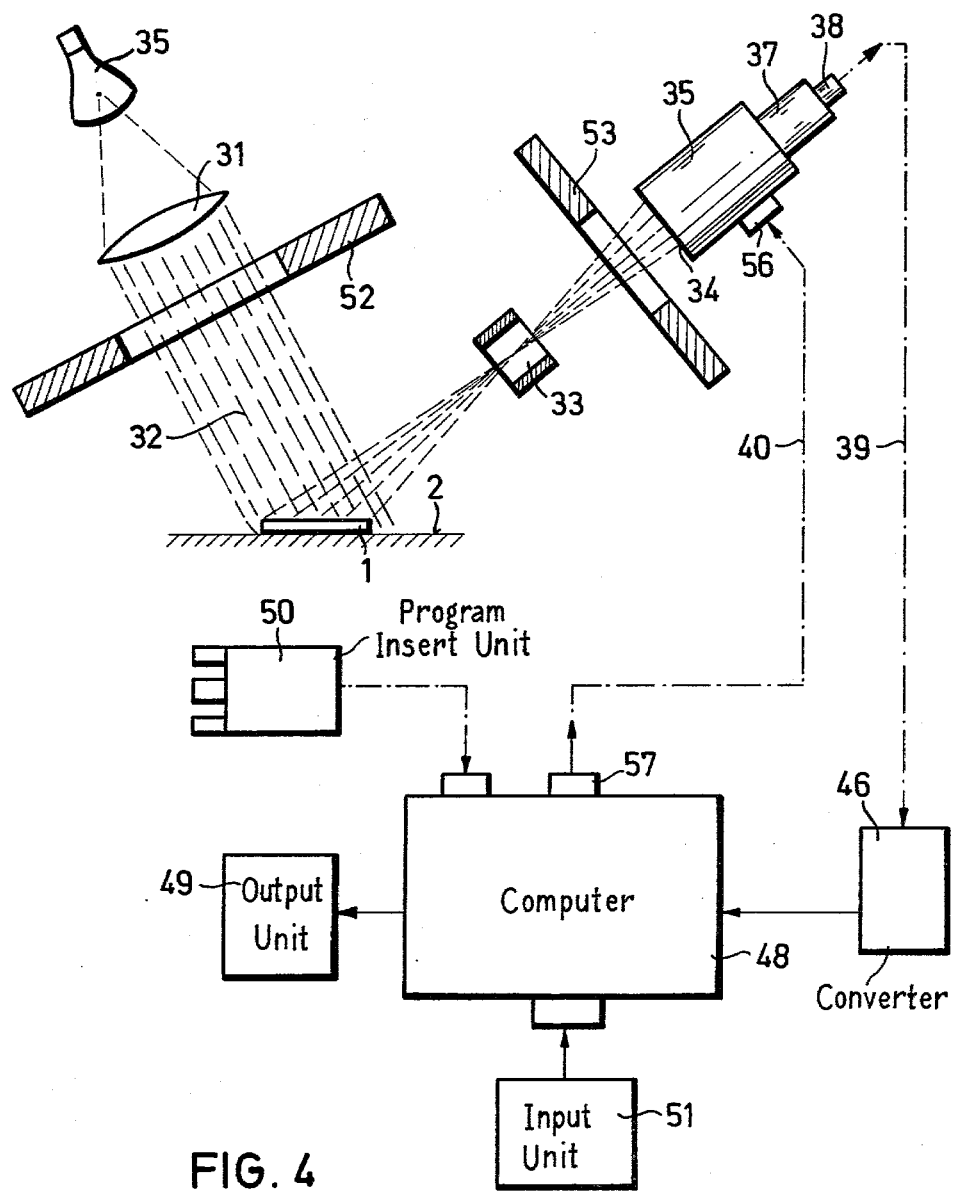
FIG. 4 shows a block diagram of the arrangement according to FIG. 2 with electronic control and evaluation device.

A substantially similar, however, functionally alternative embodiment of the apparatus is shown in FIG. 2. In this connection, the object 1 on the base 2 is irradiated by a source of light 30 whose light is concentrated through the optical device 31 on the object 1. The path of radiation of the light encountering the object 1 is indicated at 32. The radiation 55 emitted by the object 1 is projected through the lens 33 of suitable, if need be changeable, focal width or length onto the picture field 34 of the photo-cathode of a photography tube 35 (Iconoscope) and thereupon a picture produced. This picture is indicated by the number 36. It is scanned with the aid of a fine beam of electrons in known manner, linewise and picturewise. The beam guidance takes place in manner likewise known per se through the magnetic fields of two pairs of deflection coils 37 positioned perpendicularly to one another, and which have sawtooth-shaped deflection currents passing therethrough. The camera 35 converts the brightness values of the picture 36 into electrical voltage signals which are supplied into the output 38 and the control line 39. The latter according to the block circuit diagram according to FIG. 4 is in effective connection with the converter 46. This converter 46 converts the electrical signals analogous to the function in the circuit diagram of FIG. 3 into computer compatible signals. The latter are imparted to the computer 48 and there correlated with the answer back signal control impulses which are received from the coupling of the control of the scanning beam of the camera tube 35. The effective connection of the control unit, which in the present case is integrated as an entity with the computer unit 48 for the steering and guidance of the beam, takes place with the aid of the pair of deflection coils 37 through the control line 40 for the input 56 of the tube 35.

The further functions of the computer 48 correspond essentially with the computer unit 18 already described with the block circuit diagram according to FIG. 3. As a result thereof, also the computer unit 48 has an output unit 49 and a program insert unit 50.

For the entry of a reference value, for example, from a data-carrier, the input unit 51 is provided. It may consist of a plate memory, a band memory or a perforated tape memory. However, it may also alternatively be an integrated portion of the computer unit or the computer memory unit, respectively.

As may be further seen from the block circuit diagrams of FIGS. 3 and 4, in the path of the electron beam 4 or of the optical bundle of rays 12, 32, respectively, color filters 52 or 53 may be connected. These color filters may, for example, serve for the adjustment of a determined intensity value or the filtering out of a monochromatic light area.

For clarity these filter arrangements 52 and 53 are shown exclusively in diagram form. They may, however, with respect to mechanical embodiments, be arranged according to desired prototypes known to the expert, for example in prototype units serviceable by remote control, or also only as replacement lenses, etc.

In a further development of the invention, a series of other different embodiments are conceivable both of the apparatus as well as also of the manner of operation.

For example, instead of a simple bright/dark receiving Video camera 35, color receiving or color photography cameras may be utilized, which can convert color shadings of the object picture into electrical signals. Such a device brings with it, of course, a correspondingly complicated connection with computer and memory units, although functioning analogously in principle. Such an arrangement makes it possible to comprehend and evaluate the color tone of a test object absolutely or in comparison with a reference color tone by Video electronic means.

Furthermore, instead of color filters 52, 53, for example, the operation may be with a so-called monochromator.

In other cases, for example, for the determination of critical ageing phenomena of the object, additionally the utilization of fluorescence indicators may be of advantage for the recognition of changes in the cell-structure due to conditions of ageing.

Furthermore, for the production of a scanning ray, with particular advantage a so-called LASER may be introduced.

Basically, the operation may also take place with other electromagnetic wave ranges, or other types of waves. For example the utilization of Röntgen rays (X-rays) may be in order in the determination of the meat/bone ratio.

Important information as to changes in tissue, however, may also be suitably learned when the operation is carried out in the microwave region or with corpuscular radiation.

A further advantageous utilization of the method according to the invention results when comparative measurements are carried out on the object with different wavelengths of the light. For example, for different cell groups such as meat/fat, there may be available wave-ranges of the same reflection intensity, and for the same cell groups there may be other wave ranges with very different reflection intensity values.

In this case, the expert receives, for example, two different measuring values by comparative consideration of the cell groups in two wave ranges clarifying the different reflection intensity in a special manner. With the aid of these two different measuring values, during utilization of the method and computation operations described above, the different portions of these cell-groups may be determined with one test object.

Although various minor modifications may be suggested by those versed in the art, it should be understood that we wish to embody within the scope of the patent warranted hereon, all such embodiments as reasonably and properly come within the scope of our contribution to the art.

We claim as our invention:

1. A method for contact-free analysis of fat/meat quality of a meat product, comprising the steps of:
    radiating the meat product with a scanning light source which creates a moving point of light on the meat product;
    detecting continuous radiation emanating from the moving point of light on the test object and periodically converting a detected continuous radiation into definite radiation values corresponding to the point of light at scanned locations on the test object;

providing reference values which are known radiation values corresponding to fat and meat portions of a reference meat product;

comparing the reference values to the definite radiation values to create a first group of the definite values corresponding to fat portions and a second group of the definite values corresponding to meat portions of the meat product; and comparing the two groups of values to determine fat/meat quality.

2. A method according to claim 1 wherein the definite radiation values of each of the two groups are summed and the two sums are compared to determine fat/meat quality.

3. A method according to claim 2 wherein the two sums are converted to a fat/meat quality ratio.

4. A method according to claim 1 wherein the definite radiation values and reference values comprise radiation intensity.

* * * * *